United States Patent [19]

Cerinic et al.

[11] Patent Number: 4,966,889
[45] Date of Patent: Oct. 30, 1990

[54] TREATMENT OF INFLAMMATORY ARTICULAR DISEASES

[75] Inventors: Marco M. Cerinic; Simone Marabini, both of Florence, Italy

[73] Assignee: Industria Farmaceutica Serono SpA, Rome, Italy

[21] Appl. No.: 116,096

[22] Filed: Nov. 3, 1987

[30] Foreign Application Priority Data

Nov. 4, 1986 [IT] Italy .................................. 48617 A/86

[51] Int. Cl.$^5$ ............................................. A61K 37/02
[52] U.S. Cl. ..................................... 514/11; 514/806; 514/825
[58] Field of Search ............................ 514/11, 806, 825

[56] References Cited

U.S. PATENT DOCUMENTS 4,585,755 4/1986 Morgan et al. ..................... 514/11
4,748,153 5/1988 Morgan et al. ..................... 514/10

OTHER PUBLICATIONS

Hamor, Principles of Medicinal Chemistry, Foye (Ed.) Lea and Febiger, Philadelphia, p. 532, 1976.
Biological Abstract vol. 81; 89079, (1986).
Biological Abstract vol. 79; 88906 (1985).

*Primary Examiner*—Johnnie R. Brown
*Assistant Examiner*—Christina Chan
*Attorney, Agent, or Firm*—Stephan P. Williams

[57] ABSTRACT

The treatment of certain inflammatory articular diseases, e.g., rheumatoid arthritis, is carried out via the use of injectable compositions containing somatostatin.

5 Claims, No Drawings

TREATMENT OF INFLAMMATORY ARTICULAR DISEASES

BACKGROUND OF THE INVENTION

The present invention relates to rheumatology. In particular, the invention relates to the use of a known substance, Somatostatin, in the treatment of rheumatic states and, particularly, inflammatory articular diseases.

Inflammatory articular diseases, both acute and chronic, characterised by a phlogistic involvement of the synovial membrane with subsequent cartilage and bone damage, are very common. The most typical inflammatory articular disease is Rheumatoid Arthritis (RA) where, as in the case of arthrosis (degenerative disease of the cartilage with possible phlogistic involvement), all the symptomatic, analgesic and anti-inflammatory drugs, and other treatments such as gold salts, anti-malaria medicines and penicillamine, are used at present with the aim of modifying the trend of the disease.

Typical articular diseases of inflammatory character are, for example, gout, Sjögren's syndrome, ankylopoietic spondilitis, intermittent hydrarthrosis, the consequences of trauma and forms of arthrosis with inflammatory involvement, as well as the above mentioned adult Rheumatoid Arthritis and its infantile and juvenile variations.

The aetiology of RA is still unknown. Various hypotheses include aetiopathogenetic events of the psychosomatic type (nervous theory), or the cause is considered to be an altered metabolism due to hepatic dysfunction (metabolic theory), or else an infective aetiopathogenesis (infectious theory), or finally, RA is classified among the diseases due to hypersensitivity (immunitary theory). The latter is the most accredited theory at present.

Symptomatic therapy of RA and, more generally, of inflammatory articular diseases, is based on medicines with antiphlogistic and analgesic properties such as cortisonics and non-steroidal anti-inflammatory drugs (NSAIDs).

Fundamental therapy is based on synthetic antimalaria drugs, e.g. chloroquine phosphate, gold salts, penicillamine and certain immunosuppressor drugs such as azathioprine and cyclophosphamide.

All the above indicated therapies, other than not being remedial therapies for inflammatory articular diseases in general, and even less in the case of RA, are also inconvenient in that they make recourse to drugs which have more or less severe side effects and often contraindications which render inadvisable their use in the treatment of many patients, especially when treatment is long-term, as is the case with this kind of disease.

Therefore, in the field of rheumatology, a great need is felt for a treatment of RA and other inflammatory articular diseases employing efficacious drugs which are substantially devoid of side-effects and contra-indications.

Somatostatin (SS) is a peptidic hormone originally studied for its inhibitory effect on secretion by the hypophysis of the growth-hormone, also known as Somatotrophin. Due to this property, SS is also known as SRIF (Somatotrophin Release Inhibiting Factor).

Originally isolated from bovine and ovine hypothalami, Somatostatin has a well known structural formula and is currently produced by chemical synthesis.

The structure of the Somatostatin cyclic tetradecapeptide is the following:

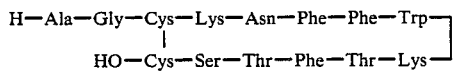

Recent studies have shown that Somatostatin is capable of inhibiting gastric secretion, endocrine pancreatic secretion, the secretion of glucagon, and of reducing the blood flow in the splanchnic area without determining significant variations in arterial pressure.

More recently, the inhibitory effect of Somatostatin on the secretion of the growth hormone has been correlated with the recognized therapeutic effect of Somatostatin in severe cases of psoriasis. The real mechanism is still the object of further studies.

Furthermore, Somatostatin has been found efficacious in the treatment of idiopathic headache, especially migraine and cluster headache.

SUMMARY OF THE INVENTION

The present invention is based on the discovery that Somatostatin constitutes an efficacious therapeutic means for the treatment of inflammatory articular diseases. The treatment is substantially devoid of side-effects, due principally to the very short half-life of this substance.

DETAILED DESCRIPTION OF THE INVENTION

Somatostatin is generally administered by continuous intravenous infusion, sometimes preceded by a bolus i.v. injection. In normal therapeutic practice, administration of this substance via i.m, s.c., and intranasal routes has also been found efficacious. For special indications, the intrathecal, peridural, intraspinal and intraventricular routes are also known.

In accordance with the present invention it has been found that the administration route of Somatostatin which gives the best results in treatment of inflammatory articular conditions, is the intra-articular route.

Therefore, a preferred object of this invention consists in injecting Somatostatin directly into the joint affected by the inflammatory pathology, that is, worded differently, the intra-articular administration of Somatostatin. The dose most commonly used in clinical trials has been 750 micrograms injected into the articular site. Both lower and higher doses than that indicated above have proved to be efficacious depending on the severity of the pathology. A range of doses capable of giving satisfactory results without incurring noticeable side-effects ranges between 500 and 1500 micrograms of Somatostatin administered by the intra-articular route.

When systemic administration is used, e.g. continuous venous infusion, the dose is usually of 250 micrograms per hour, and duration varies according to the therapeutic results obtained.

Somatostatin is normally available in ampoules or vials of the lyophilized product containing the peptide and an inert excipient such as lactose or mannitol. The product used in the clinical trials which will be described further on, is available on the market under the trademark "STILAMIN" and is manufactured by the assignee of the present patent application. It is understood that any pharmaceutically acceptable form of Somatostatin is comprised in the ambit of the present invention, whose inventive aspect is essentially based on the discovery that Somatostatin, up until now recognised useful in diverse therapeutic applications, has resulted surprisingly efficacious in the treatment of Rheumatoid Arthritis and other inflammatory articular diseases.

Clinical efficacy of Somatostatin was verified by means of a double-blind trial versus placebo.

17 patients affected by polyarticular RA were selected for the trial. Each patient was informed about the experimental nature of the treatment. The articular site chosen for the study was the knee.

In accordance with the double-blind procedure (Somatostatin versus placebo), 10 patients were treated with Somatostatin ("STILAMIN", 750 micrograms) injected inside the knee joint.

Clinical observations were carried out at time 0, each 10 minutes of the first hour, than at hourly intervals for 3 hours. A further evaluation was made after one week; during the period between the treatment and the evaluation on the seventh day, the patients filled out a table for selfevaluation. Parameters chosen were Ritchie's Index and Huskisson's Scale of Pain, evaluation of pain being made when walking, upon flexion and supine.

For comparison, 7 patients underwent intra-articular injection with placebo dissolved in 2 ml of physiological solution.

Ritchie's Index was evaluated by the clinician during direct examination of the joint by compression with the hand. The meaning of the scale is as follows:

0 = no pain
1 = pain
2 = pain and grimace
3 = pain, grimace and retraction.

The scale of Huskisson, the other evaluation criterium used in the trial, is an analogic scale of measuring pain with subjective evaluation from 1 to 10.

The following Tables summarize the results obtained in the 10 patients treated with SS (Table 1) and, for comparison, in the 7 placebo treated patients (Table 2).

TABLE I

| | | Patients treated with Somatostatin | | | | |
|---|---|---|---|---|---|---|
| | | RITCHIE'S INDEX | | PAIN LEVEL (HUSKISSON) | | |
| Case No. | Initials | Before treatment | 7 days after treatment | Position[1] | Before treatment | 3 hours after treatment |
| 1 | A. T. | 3 | 1 | S | 3 | 0,7 |
| | | | | F | 6 | 0,7 |
| | | | | W | 6 | 0,7 |
| 2 | C. A. | 2 | 1 | S | 4 | 0,1 |
| | | | | F | 5 | 1 |
| | | | | W | 6 | 2 |
| 3 | F. E. | 3 | 2 | S | 3 | |
| | | | | F | 7 | 2 |
| | | | | W | 10 | 4,2 |
| 4 | C. G. | 1 | 0 | S | | |
| | | | | F | | |
| | | | | W | 7-8 | 2 |
| 5 | B. G. | 1 | 0 | S | 2 | 0,1 |
| | | | | F | 4 | 0,1 |
| | | | | W | 6 | 0,1 |
| 6 | C. G. | 1 | 0 | S | 2 | 0 |
| | | | | F | 4 | 0 |
| | | | | W | 4 | 0,1 |
| 7 | B. M. | 3 | 0 | S | 3 | 0,1 |
| | | | | F | 8 | 0,1 |
| | | | | W | 8 | 0,1 |
| 8 | G. M. | 2 | 1 | S | 7 | 0,4 |
| | | | | F | 8 | 0,4 |
| | | | | W | 8 | 0,4 |
| 9 | R. A. | 2 | 0 | S | 2 | 0,1 |
| | | | | F | 8 | 0,1 |
| | | | | W | 8 | 0,1 |
| 10 | D. L. | 3 | 1 | S | 3 | 0,1 |
| | | | | F | 8 | 0,1 |
| | | | | W | 7 | 0,1 |

[1] S = Supine
F = Flexion
W = Walking

TABLE 2

| | | Patients treated with placebo | | | | |
|---|---|---|---|---|---|---|
| | | RITCHIE'S INDEX | | PAIN LEVEL (HUSKISSON) | | |
| Case No. | Initials | Before treatment | 7 days after treatment | Position[1] | Before treatment | 3 hours after treatment |
| 1 | F. S. | 3 | 3 | S | 5 | 4,4 |
| | | | | F | 6 | 4,8 |
| | | | | W | 6 | 5 |
| 2 | G. M. | 3 | 3 | S | | |
| | | | | F | 8 | 7 |
| | | | | W | 8 | 7 |
| 3 | A. L. | 3 | 2 | S | 3 | 4 |
| | | | | F | 8 | |
| | | | | W | 9 | |
| 4 | F. R. | 2 | 1-2 | S | 4 | |

TABLE 2-continued

| | | Patients treated with placebo | | | | |
|---|---|---|---|---|---|---|
| | | RITCHIE'S INDEX | | PAIN LEVEL (HUSKISSON) | | |
| Case No. | Initials | Before treatment | 7 days after treatment | Position[1] | Before treatment | 3 hours after treatment |
| | | | | F | 7 | |
| | | | | W | 7 | 7 |
| 5 | B. A. | 3 | 3 | S | 4 | |
| | | | | F | 6 | 6 |
| | | | | W | 8 | 8 |
| 6 | C. E. | 2 | 2 | S | 2 | |
| | | | | F | 8 | 4 |
| | | | | W | 7 | 5 |
| 7 | A. Q. | 2 | 2 | S | 2 | |
| | | | | F | 7 | 5,4 |
| | | | | W | 7 | 5,4 |

[1]S = Supine
F = Flexion
W = Walking

As can be seen from the Tables, in the patients treated with Somatostatin ("STILAMIN" Serono) an evident and rapid reduction of pain upon flexion and walking, as well as when at rest, was observed, and this was maintained up to the seventh day from administration. Ritchie's Index, which generally diminished already one hour after treatment, also maintained its level on the seventh day.

As to the placebo-treated control group, despite the occurrence of concomitant treatments with non-steroidal anti-inflammatory drugs or cortisone (for ethical reasons), no significant improvements were demonstrated.

The following Tables show more detailed data with reference to the same patients of both groups, i.e. treated with Somatostatin (Table 3), and with placebo (Table 4). These data constitute a useful complement to the essential results reported in the previous Tables 1 and 2.

TABLE 3

| Case No. | Initials | Position | Level of Pain after treatment with Somatostatin | | | | | | | | | | | | | | | | |
|---|---|---|---|---|---|---|---|---|---|---|---|---|---|---|---|---|---|---|---|
| | | | | | | | | | | | 1st day | | 2nd day | | 3rd day | | 4th day | |
| | | | 10' | 20' | 30' | 40' | 50' | 1 h | 2 h | 3 h | a.m. | p.m. | a.m. | p.m. | a.m. | p.m. | a.m. | p.m. |
| 1 | A. T. | S | 0,1 | 0,1 | 0,1 | 0,1 | 0,1 | 0,1 | 0,7 | 0,7 | 1 | 1 | 1 | 1 | 1 | 2 | 1 | 2 |
| | | F | 1 | 1 | 1 | 1 | 0,9 | 0,9 | 0,7 | 0,7 | 1 | 1 | 1 | 1 | 1 | 2 | 1 | 2 |
| | | W | 1 | 1 | 1 | 1 | 0,9 | 0,9 | 0,7 | 0,7 | 1 | 1 | 1 | 1 | 1 | 2 | 1 | 2 |
| 2 | C. A. | S | 1 | 1 | 0,1 | | | 0,5 | 0,1 | 0,1 | 0,5 | 1 | 1 | 0,5 | 0,5 | 0,5 | 0,5 | 0,5 |
| | | F | 1,6 | 1,6 | 2 | | | 0,2 | 1 | 1 | 1 | 1 | 0,5 | 2 | 2 | 1 | 2 | 1 |
| | | W | 2 | 2 | 2 | | | 2,2 | 2 | 2 | 2 | 1 | 2 | 1 | 1 | 2 | 3 | 2 |
| 3 | F. E. | S | | | | | | | | | 2 | 2 | 2 | 2 | 2 | 2 | 2 | 2 |
| | | F | 7 | 6 | 4,9 | 3,5 | 3 | 3 | 2 | 2 | 3 | 3 | 3 | 4 | 4 | 4 | 4 | 4 |
| | | W | 8 | 7,9 | 5,8 | 4,9 | 4,5 | 4,2 | 4,2 | 4,2 | 5 | 5 | 5 | 5 | 5 | 6 | 6 | 6 |
| 4 | C. G. | S | | | | | | | | | | | | | | | | |
| | | F | | | | | | | | | | | | | | | | |
| | | W | 7,5 | 7 | 6,5 | 6,1 | 5,8 | 5,1 | 3 | 2 | | 2,8 | 1,8 | 2 | 1,9 | 1,2 | 1 | 1 |
| 5 | B. G. | S | 0,1 | 0,1 | 0,1 | 0,1 | 0,1 | 0,1 | 0,1 | 0,1 | 0,1 | 0,1 | | | | | | |
| | | F | 0,1 | 0,1 | 0,1 | 0,1 | 0,1 | 0,1 | 0,1 | 0,1 | 0,1 | 0,1 | | 0,5 | 1,2 | 0,8 | 0,8 | 0,9 |
| | | W | 0,1 | 0,1 | 0,1 | 0,1 | 0,1 | 0,1 | 0,1 | 0,1 | 0,1 | 0,1 | 0,1 | 0,1 | 0,1 | 0,1 | 0,1 | 0,1 |
| 6 | C. G. | S | 0,1 | 0 | 0 | 0 | 0 | 0 | 0 | 0 | | | | | | | | |
| | | F | 0 | 0 | 0 | 0 | 0 | 0 | 0 | 0 | | 0,3 | 0,3 | 0,3 | 0,3 | 0,5 | 0,5 | 0,5 |
| | | W | 0,1 | 0,1 | 0,1 | 0,1 | 0,1 | 0,1 | 0,1 | 0,1 | | | | | | | | |
| 7 | B. M. | S | 0,1 | 0,1 | 0,1 | 0,1 | 0,1 | 0,1 | 0,1 | 0,1 | | 3,2 | 0,1 | 0,1 | 0,1 | 0,8 | 1,2 | 0,8 |
| | | F | 3 | 0,1 | 0,1 | 0,1 | 0,1 | 0,1 | 0,1 | 0,1 | | 0,1 | 0,1 | 0,1 | 0,1 | 0,8 | 1,2 | 0,8 |
| | | W | 3 | 0,1 | 0,1 | 0,1 | 0,1 | 0,1 | 0,1 | 0,1 | | 0,1 | 0,1 | 0,1 | 0,1 | 0,8 | 1,2 | 0,8 |
| 8 | G. M. | S | 0,4 | 0,4 | 0,4 | 0,4 | 0,4 | 0,4 | 0,4 | 0,4 | 0,6 | 0,8 | 0,1 | 0,1 | 0,2 | 0,2 | 0,2 | 0,2 |
| | | F | 0,4 | 0,4 | 0,4 | 0,4 | 0,4 | 0,4 | 0,4 | 0,4 | 0,6 | 0,8 | 0,1 | 0,1 | 0,2 | 0,2 | 0,2 | 0,2 |
| | | W | 0,4 | 0,4 | 0,4 | 0,4 | 0,4 | 0,4 | 0,4 | 0,4 | 0,6 | 0,8 | 0,1 | 0,1 | 0,2 | 0,2 | 0,2 | 0,2 |
| 9 | R. A. | S | 0,1 | 0,1 | 0,1 | 0,1 | 0,1 | | 0,1 | 0,1 | | 0,1 | 0,1 | 0,1 | 0,1 | 0,1 | 0,1 | 0,6 |
| | | F | 0,1 | 0,1 | 0,1 | 0,1 | 0,1 | | 0,1 | 0,1 | | 0,1 | 0,1 | 0,1 | 0,1 | 0,1 | 0,1 | 0,6 |
| | | W | 0,1 | 0,1 | 0,1 | 0,1 | 0,1 | | 0,1 | 0,1 | | 0,1 | 0,1 | 0,1 | 0,1 | 0,1 | 0,1 | 0,6 |
| 10 | D. L. | S | 0,1 | 0,1 | 0,1 | 0,1 | 0,1 | | 0,1 | 0,1 | | 0,2 | 0,2 | 0,2 | 0,2 | 0,9 | 0,2 | 0,9 |
| | | F | 2 | 0,4 | 0,1 | 0,1 | 0,1 | | 0,1 | 0,1 | | 0,2 | 0,2 | 0,2 | 0,2 | 0,9 | 0,2 | 0,9 |
| | | W | 3 | 1 | 0,1 | 0,1 | 0,1 | | 0,1 | 0,1 | | 0,2 | 0,2 | 0,2 | 0,2 | 0,9 | 0,2 | 0,9 |

| Case No. | Initials | Position | Level of Pain after treatment with Somatostatin | | | | | |
|---|---|---|---|---|---|---|---|---|
| | | | 5th day | | 6th day | | 7th day | |
| | | | a.m. | p.m. | a.m. | p.m. | a.m. | p.m. |
| 1 | A. T. | S | 1 | 2 | 1 | 2 | 2 | 2 |
| | | F | 1 | 2 | 1 | 2 | 2 | 2 |
| | | W | 1 | 2 | 1 | 2 | 2 | 2 |
| 2 | C. A. | S | 1 | 0,5 | 0,5 | 0,5 | 0,5 | 0,5 |
| | | F | 2 | 1 | 1 | 1 | 1 | 1 |
| | | W | 2 | 2 | 1 | 1 | 1 | 2 |
| 3 | F. E. | S | 2 | 2 | 2 | 2 | 2 | 2 |
| | | F | 3 | 3 | 4 | 4 | 4 | 4 |

TABLE 3-continued

| | | | | | | | | |
|---|---|---|---|---|---|---|---|---|
| 4 | C. G. | W | 6 | 6 | 6 | 6 | 6 | 6 |
| | | S | | | | | | |
| | | F | | | | | | |
| 5 | B. G. | W | 1,2 | 1,3 | 1,2 | 1 | 1 | 1,2 |
| | | S | | | | | | |
| | | F | 0,9 | 0,9 | 0,9 | 0,9 | 0,9 | 0,9 |
| 6 | C. G. | W | 0,1 | 0,1 | 0,1 | 0,1 | 0,1 | 0,1 |
| | | S | | | | | | |
| | | F | 0,5 | 0,5 | 0,5 | 0,5 | 0,5 | 0,5 |
| 7 | B. M. | W | | | | | | |
| | | S | 0,8 | 0,8 | 0,8 | 1,2 | 0,8 | 0,8 |
| | | F | 0,8 | 0,8 | 0,8 | 1,2 | 0,8 | 0,8 |
| 8 | G. M. | W | 0,8 | 0,8 | 0,8 | 1,2 | 0,8 | 0,8 |
| | | S | 0,9 | 0,9 | 0,9 | 0,9 | 0,9 | 0,9 |
| | | F | 0,9 | 0,9 | 0,9 | 0,9 | 0,9 | 0,9 |
| | | W | 0,9 | 0,9 | 0,9 | 0,9 | 0,9 | 0,9 |
| 9 | R. A. | S | 0,1 | 0,1 | 0,1 | 0,1 | 0,1 | 0,1 |
| | | F | 0,1 | 0,1 | 0,1 | 0,1 | 0,1 | 0,1 |
| | | W | 0,1 | 0,1 | 0,1 | 0,1 | 0,1 | 0,1 |
| 10 | D. L. | S | 0,2 | 0,9 | 0,2 | 1,9 | 1 | 1,9 |
| | | F | 0,2 | 0,9 | 0,2 | 1,9 | 1 | 1,9 |
| | | W | 0,2 | 0,9 | 0,2 | 1,9 | 1 | 1,9 |

TABLE 4

| | | | Level of Pain after treatment with Placebo | | | | | | | | | | | | | | | |
|---|---|---|---|---|---|---|---|---|---|---|---|---|---|---|---|---|---|---|
| Case | | | | | | | | | | 1st day | | 2nd day | | 3rd day | | 4th day | | |
| No. | Initials | Position | 10' | 20' | 30' | 40' | 50' | 1 h | 2 h | 3 h | a.m. | p.m. | a.m. | p.m. | a.m. | p.m. | a.m. | p.m. |
| 1 | F. S. | S | 2 | 2 | 2 | | | 3 | 4 | 4,4 | 5 | 5 | 4 | 4,8 | 4 | 4 | 4 | 4 |
| | | F | 4 | 4 | 4 | | | 4 | 4,8 | 4,8 | 5 | 5 | 4 | 4,8 | 4 | 4 | 4 | 4 |
| | | W | 5 | 5 | 5 | | | 5 | 5 | 5 | 5 | 5 | 4 | 4,8 | 4 | 4 | 4 | 4 |
| 2 | G. M. | S | | | | | | | | | | 7 | 6 | 7 | 6 | 8 | 8 | 8 |
| | | F | 8 | 7 | 7 | 6 | 6 | 6 | 7 | 7 | | 7 | 6 | 7 | 6 | 8 | 8 | 8 |
| | | W | 8 | 7 | 7 | 6 | 6 | 6 | 7 | 7 | | 7 | 6 | 7 | 6 | 8 | 8 | 8 |
| 3 | A. L. | S | 3 | 2 | 2 | 2 | 2 | 2 | 3 | 4 | | | 2 | 3 | | 3 | | 3 |
| | | F | | | | | | | | | | | | | | | | |
| | | W | | | | | | | | | | | | | | | | |
| 4 | F. R. | S | | | | | | | | | | | | | | | | |
| | | F | | | | | | | | | | | | | | | | |
| | | W | 7 | 7 | 6,5 | 6 | 5,5 | 5,5 | 7 | 7 | 7 | 7 | 7 | 7 | 7 | 6 | 6 | 5 |
| 5 | B. A. | S | | | | | | | | | | | | | | | | |
| | | F | 6 | 6 | 6 | 6 | 6 | 6 | 6 | 6 | | 6 | 6 | 6 | 6 | 6 | 6 | 6 |
| | | W | 8 | 8 | 8 | 8 | 8 | 8 | 8 | 8 | | 8 | 8 | 8 | 8 | 8 | 8 | 8 |
| 6 | C. E. | S | | | | | | | | | | | | | | | | |
| | | F | 7 | 6 | 5 | 5 | 4 | 4 | 4 | 4 | 4 | 6 | 7 | 7 | 7 | 7 | 4 | 6 |
| | | W | 8 | 7 | 6 | 6 | 6 | 6 | 5 | 5 | 5 | 7 | 8 | 8 | 8 | 8 | 5 | 6 |
| 7 | A. Q. | S | | | | | | | | | | | | | | | | |
| | | F | 7 | 7 | 7 | 7 | 6,2 | 6,2 | 5,4 | 5,4 | | 6 | 6 | 5 | 5 | 6 | 7 | 7 |
| | | W | 7 | 7 | 7 | 7 | 6,2 | 6,2 | 5,4 | 5,4 | | 6 | 6 | 5 | 5 | 6 | 7 | 7 |

| | | | Level of Pain after treatment with Placebo | | | | | |
|---|---|---|---|---|---|---|---|---|
| Case | | | 5th day | | 6th day | | 7th day | |
| No. | Initials | Position | a.m. | p.m. | a.m. | p.m. | a.m. | p.m. |
| 1 | F. S. | S | 3,2 | 3,8 | 4,8 | 5,8 | 5,8 | 5,8 |
| | | F | 3,2 | 3,8 | 4,8 | 5,8 | 5,8 | 5,8 |
| | | W | 3,2 | 3,8 | 4,8 | 5,8 | 5,8 | 5,8 |
| 2 | G. M. | S | 8 | 8,9 | 8 | 8,9 | 8,9 | 8,9 |
| | | F | 8 | 8,9 | 8 | 8,9 | 8,9 | 8,9 |
| | | W | 8 | 8,9 | 8 | 8,9 | 8,9 | 8,9 |
| 3 | A. L. | S | | 4 | 3 | 4 | | 5 |
| | | F | | | | | | |
| | | W | | | | | | |
| 4 | F. R. | S | | | | | | |
| | | F | | | | | | |
| | | W | 5 | 5 | 5 | 5 | 5 | 5 |
| 5 | B. A. | S | | | | | | |
| | | F | 5 | 6 | 5 | 5 | 5 | 5 |
| | | W | 8 | 8 | 8 | 8 | 7 | 7 |
| 6 | C. E. | S | | | | | | |
| | | W | 4 | 7 | 7 | 7 | 7 | 6 |
| | | W | 5 | 8 | 8 | 8 | 8 | 7 |
| 7 | A. Q. | S | | | | | | |
| | | F | 7 | 7 | 6 | 6 | 7 | 7 |
| | | W | 7 | 7 | 6 | 6 | 7 | 7 |

With reference to each of the clinical cases taken into consideration, supplied below are the particulars relevant to diagnosis, evaluation of efficacy of therapies in course prior to treatment (Nil, Scarce, Good, Excellent), and finally the clinical observations after treatment with Somatostatin (SS) or with Placebo (PL).

Case 1—SS.

Initials: A. T. Age: 65 Sex: F
Diagnosis: Polyarticular R.A.
Duration of Disease: 30 yrs
The patient had undergone multiple basic therapies (gold salts i.m., gold salts per os, penicillamine, etc.) which she had to suspend due to severe side-effects. Furthermore, the patient was affected by severe iatrogenic osteoporosis (steroids).
Present therapy: Piroxicam 20 mg and 6-alpha-methylprednisolone 8 mg.
Efficacy: scarce
Observations: The patient responded immediately to the local injective therapy and the effect was maintained up to the final control on the seventh day.

Case 2—SS

Initials: C. A. Age: 40 Sex: F.
Diagnosis: Polyarticular R.A.
Duration of Disease: 15 years.
The patient had been under treatment with gold salts i.m. for 2 years, but such therapy was not satisfactory. Infiltration was decided upon due to the persistent pain and presence of fluid at the knee.
Present therapy: Piroxicam 20 mg.
Efficacy: Scarce
Observations: The patient experienced good immediate improvement (despite the presence of fluid) after the intra-articular injection. On the seventh day the patient was able to walk without pain despite the continuous presence of fluid.

Case 3—SS

Initials: F. E. Age: 66 Sex: F.
Diagnosis: Polyarticular R.A.
Duration of disease: 25 years.
The patient had been submitted to various basic therapies without success.
Infiltration was decided upon due to the presence of conspicuous fluid and mechanical pain.
Present therapy: Piroxicam 20 mg; 6-alpha-methylprednisolone 4 mg.
Efficacy: Scarce.
Observations: Excellent immediate response, maintained over a period of time (checked on 7th day).

Case 4—SS

Initials: C. G. Age: 72 Sex: F.
Diagnosis: Polyarticular R.A.
Duration of disease: 23 years.
Patient under therapy with gold salts per os with scarce results. She is diabetic and requires daily insulin. Despite prior clinical synoviectomy the knee was painful, especially when under force.
Present therapy: Diclofenac 50 mg.
Efficacy : Scarce.
Observations: The patient experienced excellent immediate response which has been maintained over a period of time.

Case 5—SS

Initials: B. G. Age: 68 Sex: M.
Diagnosis: Polyarticular R.A.
Duration of disease: 16 years.
The patient was forced to suspend basic therapies due to side-effects. Therapy of injection into the knee was chosen in consideration of the pain and the presence of fluid (prior clinical synoviectomy).
Present therapy: Piroxicam 20 mg.
Efficacy: Scarce.
Observations: Immediate response, excellent on the 7th day.

Case 6—SS

Initials: C. G. Age: 62 Sex: F.
Diagnosis: Polyarticular R.A.
Duration of disease: 7 years.
Scarce results obtained with gold salts treatment per os. Knee slightly tumefied but with the presence of fluid.
Present therapy: Naproxen 500×2 per day.
Efficacy: Good.
Observations: Immediate response to the injection, excellently maintained up to the 7th day.

Case 7—SS

Initials: B. M. Age: 50 Sex: F.
Diagnosis: Polyarticular R.A.
Duration of disease: 4 years.
An especially aggressive form with little efficacy from basic therapies. Injection was decided due to pain, especially under force.
Present therapy: Diclofenac 50.
Efficacy: Scarce.
Observation: Excellent, immediate response, maintained until the 7th day.

Case 8—SS

Initials: G. M. Age: 68 Sex: M.
Diagnosis: Polyarticular R.A.
Duration of disease: 5 years.
Particularly aggressive form, patient under therapy with gold salts per os. Knee tumefied with conspicuous fluid, extremely painful.
Present therapy: Diclofenac 50.
Efficacy: Scarce.
Observations: Excellent, immediate response, maintained up to the 7th day.

Case 9—SS

Initials: R. A. Age: 74 Sex: M.
Diagnosis: Polyarticular R.A.
Duration of disease: 12 years.
Under treatment with Hydroxychloroquine with scarce results. Knee strongly tumefied, pain mainly when under force.
Present therapy: Piroxicam 20 mg.
Efficacy: Scarce.
Observations: Excellent, immediate response, maintained also on the 7th day.

Case 10—SS

Initials: D. L. Age: 48 Sex: F.
Diagnosis: Polyarticular R.A.
Duration of disease: 7 years.
Under treatment with gold salts per os. Scarce results. Tumefied knee with considerable fluid; acute pain.
Present therapy: Thiaprophenic Acid 250.
Efficacy: Nil.
Observations: Good immediate response; excellent on 7th day of observation.

Case 1—PL

Initials: F. S. Age: 57 Sex: F.
Diagnosis: Polyarticular R.A.
Duration of disease: 6 years.
Patient under treatment with gold salts i.m. with good results but suffering from persistent gonarthritis, insensitive to basic therapy.
Present therapy: Naproxene 500×2.
Efficacy: Good.
Observations: Slight immediate response which did not last longer than three hours, nor was evident on the 7th day.

Case 2—PL

Initials: G. M. Age: 55 Sex: M.
Diagnosis: Polyarticular R.A.
Duration of disease: 9 years.
The patient responded well to basic therapy but due to side effects was forced to suspend.
An elevated degree of spontaneous pain and the presence of fluid at the knee.
Present therapy: Naproxene 500×2.
Efficacy: Scarce.
Observations: Only slight response both immediately after injection and over the period of time.

Case 3—PL

Initials: A. L. Age: 50 Sex: F.
Diagnosis: Polyarticular R.A.
Duration of disease: 15 years.
Aggressive and damaging form of the disease with severe compromise of both knees (fluid and instability). Scarce results obtained from basic therapy.
Present therapy: Piroxicam 20 mg.
Efficacy: Scarce.
Observations: Slight initial improvement; no improvement on the 7th day.

Case 4—PL

Initials: F. R. Age: 52 Sex: F.
Diagnosis: Polyarticular R.A.
Duration of disease: 12 years.
Particularly aggressive form, scarce response to basic therapy. Gonarthritis with fluid and pain when under force.
Present therapy: Thiaprophenic Acid.
Efficacy: Scarce.
Observations: No response, either immediately or 7 days later.

Case 5—PL

Initials: B. A. Age: 51 Sex: M.
Diagnosis: Polyarticular R.A.
Duration of disease: 9 years.
Oligo-articular form with prevalent involvement of the knee.
Present therapy: Piroxicam 20 mg.
Efficacy: Scarce.
Observations: No response, either immediate or at the 7th day.

Case 6—PL

Initials: C. E. Age: 60 Sex: F.
Diagnosis: Polyarticular R.A.
Duration of disease: 21 years.
Patient underwent various basic therapies without success.
Present therapy: 6-alpha-methylprednisolone 8 mg.
Efficacy: Scarce.
Observations: Slight initial response with rebound on the 3rd day and disappearance of benefit on the 7th.

Case 7—PL

Initials: A. Q. Age: 55 Sex: M.
Diagnosis: Polyarticular R.A.
Duration of disease: 8 years.
Disease still in acute phase despite basic therapy with Hydroxychloroquine. Knee tumified with presence of fluid.
Present therapy: Ketoprofene.
Efficacy: Nil.
Observations: No significant results.

In conclusion, treatment with Somatostatin gave excellent clinical results. In fact, after only a few minutes from the injection the patients noticed a considerable reduction of subjective pain, whether provoked (Ritchie's Index) or upon walking, flexion and at rest in supine position (level of pain according to Huskisson). Benefit of the therapy was still appreciable at the check on the 7th day.

No verifiable clinical side effects were manifested in the patients treated with Somatostatin, either at the moment of administration or in the following days.

In uncontrolled tests carried out in fewer patients, Somatostatin was found to be efficacious even by the classical administration route via i.v. infusion at doses of 250 mcg. per hour for 24–72 hours.

It is obvious that many modifications and variations may be made to the therapeutic regime described above without departing from the spirit and scope of the invention.

The examples described above are for the purpose of illustration only and are in no way to be construed as limiting to the invention itself.

We claim:

1. A method of treating rheumatoid arthritis in mammals comprising the administration thereto of a composition containing somatostatin.

2. The method of claim 1 wherein the composition is administered via intra-articular injection.

3. The method of claim 1 wherein the composition is administered via intra-articular injection at a dose ranging from 500 to 1500 mcg of somatostatin.

4. The method of claim 1 wherein the composition is administered via continuous intravenous infusion.

5. The method of claim 1 wherein the composition is administered via continuous intravenous infusion at a dosage of 250 mcg somatostatin per hour.

* * * * *